United States Patent [19]

Rich

[11] Patent Number: 4,709,054

[45] Date of Patent: * Nov. 24, 1987

[54] SILYLATION METHOD AND ORGANIC SILANES MADE THEREFROM

[75] Inventor: Jonathan D. Rich, Rexford, N.Y.

[73] Assignee: General Electric Company, Schenectady, N.Y.

[*] Notice: The portion of the term of this patent subsequent to Aug. 5, 2003 has been disclaimed.

[21] Appl. No.: 765,089

[22] Filed: Aug. 13, 1985

Related U.S. Application Data

[63] Continuation-in-part of Ser. No. 647,332, Sep. 4, 1984, abandoned.

[51] Int. Cl.$^4$ ............ C07F 7/08; C07F 7/10; C07F 7/18; C07D 307/77
[52] U.S. Cl. ............ 549/214; 556/431; 556/432; 556/435; 556/415; 556/416; 556/417; 556/422; 556/436; 556/443; 556/444; 556/450; 556/452; 556/453; 556/456; 556/460; 556/468; 556/426; 556/427; 548/406; 548/473
[58] Field of Search ............ 549/214; 548/406, 473; 556/426, 431, 427, 432, 435, 415, 416, 417, 422, 436, 443, 444, 450, 452, 453, 456, 460, 468

[56] References Cited

U.S. PATENT DOCUMENTS

| | | | |
|---|---|---|---|
| 2,562,000 | 7/1951 | Sveda | 260/46.5 |
| 3,182,073 | 5/1965 | Lonerini | 549/214 X |
| 3,299,101 | 1/1967 | Tocker | 549/214 |
| 3,391,109 | 7/1968 | Wilkus et al. | 556/436 X |
| 3,855,241 | 12/1974 | Wilkus et al. | 549/214 X |
| 4,072,710 | 2/1978 | Coll | 549/214 X |
| 4,528,495 | 3/1986 | Soula et al. | 556/468 |

OTHER PUBLICATIONS

"Chem. Abs.", Bailey et al., 56, (1962), p. 15548.
Bailey et al., "Chem. Abs.", 57, (1962), p. 13804.
Vainshtein et al., "Chem. Abs.", 83, (1975), #59018d.
Vainshtein et al., "Chem. Abs.", 77, (1972), #6002p, #6006.
"J. Org. Chem.", 38, No. 25, p. 4271, 1973.
Preparation of Substituted Benzoyltrimethylsilanes by the Palladium-Catalyzed Silylation of Substituted Benzoyl Chlorides with Hexamethyldisilane, Yamamoto, Tetrahedron Letters, vol. 21, pp. 1653–1656.
Synthesis of Some Methyldisilanes Containing Functional Groups, Makoto et al., J. of Org. Chem., 21, 1264 (1956).
Preparation of Dimethyltetramethoxydisilane from the Disilane Fraction, Watanabe, JOMC 128 (1977) 173–175.
Hydrogen–Halogen Exchange Between Silanes and Triphenylmethyl Halides, Corey et al., JACS 85, 2430 (1963).

*Primary Examiner*—Paul F. Shaver
*Attorney, Agent, or Firm*—William A. Teoli; James C. Davis, Jr.; J. Magee, Jr.

[57] ABSTRACT

A method is provided for silylating organic substrates, utilizing a halogenated polysilane, such as 1,1,2,2-tetrachloro dimethyldisilane and an aromatic acyl halide, for example, trimellitic anhydride acid chloride in the presence of a transition metal catalyst.

30 Claims, No Drawings

SILYLATION METHOD AND ORGANIC SILANES MADE THEREFROM

CROSS REFERENCE TO RELATED APPLICATIONS

This application is a continuation-in-part of my copending application Ser. No. 647,332, filed Sept. 4, 1984, now abandoned, for Silylation Method. Reference is also made to copending application Ser. No. 647,301, filed Sept. 4, 1984, now abandoned, for Method for Making Silylated Aromatic Imides, where both applications are assigned to the same assignee as the present invention and incorporated herein by reference.

BACKGROUND OF THE INVENTION

Prior to the present invention, as shown by Yamamoto et al., Tetrahedron Letters, 1653 (1980), activated aromatic acyl halide such as p-nitrobenzoyl chloride, can be converted to the corresponding aromatic silane with loss of carbon monoxide as a result of a decarbonylation reaction utilizing hexamethyldisilane as the silylating reactant. However, it also was found that the silylation of the aromatic nucleus was only partially successful, as the major product of the Yamamoto et al. reaction was the corresponding aromatic silyl ketone.

The present invention is based on my discovery that if in place of the hexamethyldisilane utilized by Yamamoto et al., there is used a halogenated polysilane, of the formula $$R(Si)_n\underset{\underset{R}{|}}{\overset{\overset{R}{|}}{Si}}-X \quad (1)$$

in reaction with an aromatic acyl halide of the formula $$R^1(CX)_m \quad (2)$$

(where the C has a double-bonded O)

in the presence of an effective amount of a transition metal catalyst as defined hereinafter, a significant yield of an organic silane is obtained having the formula $$R^1[-Si(R^2)_2X]_m \quad (3)$$

where X is a halogen radical, R is selected from X, hydrogen, $C_{(1-13)}$ monovalent hydrocarbon radicals, substituted $C_{(1-13)}$ monovalent hydrocarbon radicals and divalent —O—, —S— radicals and mixtures thereof, which can form ≡SiOSi≡ and ≡SiSSi≡ connecting groups, $R^1$ is a $C_{(6-20)}$ monovalent or polyvalent aromatic organic radical selected from hydrocarbon radicals and substituted hydrocarbon radicals, $R^2$ is selected from $C_{(1-13)}$ monovalent hydrocarbon radicals, substituted $C_{(1-13)}$ monovalent hydrocarbon radicals, and mixtures thereof included within R, n is an integer equal to 1 to 50 inclusive, and m is an integer equal to 1 to 4 inclusive.

STATEMENT OF THE INVENTION

There is provided by the present invention a method for making organic silanes which comprises
(A) effecting reaction between aromatic acyl halide of formula (2) and halogenated polysilane of formula (1) in the presence of an effective amount of a transition metal catalyst and
(B) thereafter recovering organic silane from the resulting mixture of (A).

Some of the aromatic acyl halides which are included within formula (2) are, for example, monofunctional aromatic acyl halide such as benzoyl chloride, trimellitic anhydride acid chloride, chlorobenzoylchloride, anisoylchloride, nitrobenzoylchloride, toluoylchloride, cyanobenzoylchloride, bromobenzoylchloride, dimethylaminobenzoylchloride, N-n-butyl trimellitic imide acid chloride, etc.

Polyfunctional aromatic polyacyl halides which are included within formula (2) are, for example, terephthaloylchloride, phthaloylchloride, isophthaloylchloride, etc.

Some aromatic silanes which are included within formula (3) are, for example, phenyldimethylchlorosilane, phenylmethyldichlorosilane, chlorophenyldimethylchlorosilane, anisyldimethylchlorosilane, nitrophenyldimethylchlorosilane, tolyldimethylchlorosilane, cyanophenyldimethylchlorosilane, 4-dimethylchlorosilylphthalic anhydride, N-n-butyl-4-dimethylchlorosilyl phthalimide, bromophenyldimethylchlorosilane, etc.

Among the polysilanes which are included within formula (1) there are, for example, chloropentamethyldisilane, 1,2-dichlorotetramethyldisilane, 1,1-dichlorotetramethyldisilane, 1,1,2-trimethyltrichlorodisilane, 1,1,2,2-tetrachlorodimethyldisilane, hexachlorodisilane, 1,2-dibromotetramethyldisilane, 1,2-difluorotetramethyldisilane, 1,1,2,2,4,4,5,5-octamethyl-1,2,4,5-tetrasilacyclohexasiloxane, 1-chlorononamethyl-tetrasil-3-oxane, 1,2-dichloro-1,2-diphenyldimethyldisilane, etc.

Radicals which can be included within R and $R^2$ of formulas (1) and (3) are, for example, $C_{(1-8)}$ alkyl radicals, for example, methyl, ethyl, propyl, butyl, pentyl, etc., chlorobutyl, trifluoropropyl, cyanopropyl, as well as monovalent aryl radicals and substituted monovalent aryl radicals as defined for $R^1$ below.

Some of the monovalent aromatic radicals and substituted aromatic radicals which can be included within $R^1$ of formulas (2) and (3) are, for example, phenyl, xylyl, tolyl, naphthyl; halogenated aromatic radicals such as chlorophenyl, dichlorophenyl, trichlorophenyl, etc., fluorophenyl, difluorophenyl, etc., bromophenyl, dibromophenyl, etc.; nitro and polynitro aromatic radicals as well as aryl ether radicals for example, anisoyl, ethoxyphenyl, propoxyphenyl, diphenylether. Additional substituted aromatic radicals which can be included within $R^1$ are for example, cyanophenyl, polycyanophenyl, as well as phthalimido radicals.

Some of the preferred organic silanes included within formula (3) are silarylene halides as shown by the following formula, $$\underset{\underset{R^3}{|}}{\overset{\overset{R^3}{|}}{XSiR^4}}-\underset{\underset{R^3}{|}}{\overset{\overset{R^3}{|}}{SiX}} \quad (4)$$

where $R^3$ include the same or different monovalent radicals and substituted monovalent radicals defined within R and $R^2$ above and radicals included within $R^4$ are $C_{(6-13)}$ divalent aromatic radicals and substituted $C_{(6-13)}$ divalent aromatic radicals such as phenylene, xylylene, tolylene, naphthelene and halogenated derivatives thereof, and X is as previously defined. A particularly preferred silarylene halide is silphenylene chloride, or 1,4-(bis-chlorodimethylsilyl)benzene. The synthesis of such silphenylene compound can be made from terephthaloyl chloride and 1,2-dichlorotetramethyldisilane as shown by the following equation:

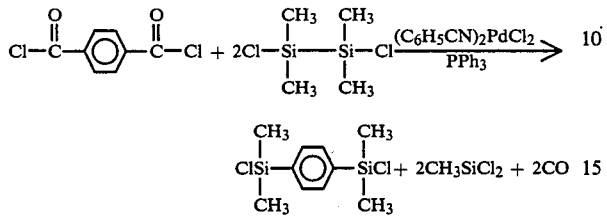

Among the transition metal catalysts which can be utilized in the practice of the present invention, there are included bisbenzonitrilepalladiumdichloride, bisacetonitrilepalladium dichloride, allylpalladiumchloride dimer, bis(triphenylphosphine)palladium dibromide, bis(triphenylphosphine)palladiumiodide, tetrakis(triphenylphosphine)palladium, palladium dichloride, bis(diphenylmethyl)phosphine palladium dichloride, palladium on carbon, palladium on silica. Additional complexes of the following metals also can be used such as complexes of rhodium, iridium, cobalt, platinum and other Group VIII metals. The preferred transition metal catalyst is bisbenzonitrile palladium dichloride.

An amine or phosphine cocatalyst such as trimethylamine, triethylamine, tributylamine, pyridine, N,N,N',N'-tetramethyl ethylenediamine,triphenylphosphine, tri-p-tolylphosphine, tri-o-anisylphosphine, trimethyl or tributylphosphine, tricyclohexylphosphine can be used to facilitate the decarbonylation.

An effective amount of transition metal catalyst is from 0.05% by weight to 0.15% by weight, based on the weight of aromatic acyl halide of formula (2). An effective amount of the cocatalyst is from 0.10% to 0.30% by weight based on the weight of aromatic acyl halide.

In the practice of the present invention, reaction is initiated between the halogenated polysilane of formula (1) and the organic acid halide of formula (2) in the presence of an effective amount of the transition metal catalyst. Reaction can be carried-out under a variety of conditions. The reactants, for example, can be heated to the desired temperature in the absence of solvent while being stirred under an inert atmosphere or a non-reactive solvent with a boiling point greater than about 100° to 300° C. For example, there can be used o-xylene, anisole, mesitylene, or non-halogenated aromatic or aliphatic solvents. It also be may possible to carry-out the reaction in the gas phase by passing the gaseous reactants over a bed containing the transition metal catalyst bound on a polymer support material. An additional procedure which can be used to carry-out the reaction is a liquid flow system where the reactants are dissolved in a hot, non-reactive solvent or if the reactants are compatible, they can be passed over a polymer bound catalyst.

Depending upon the value of n in formula (2) for the organic acid halide and whether the halogenated polysilane is a monofunctional or polyfunctional halopolysilane, the molar proportions of the halogenated polysilane and the organic acid halide can vary widely. There should be used sufficient halogenated polysilane to provide at least two gram atoms of silicon of the halogenated polysilane per mole of the organic acyl halide.

Temperatures which can be utilized in effecting reaction between the halogenated polysilane and the organic acyl halide are, for example, 110° to 300° C. and preferably 135° to 145° C. depending upon the nature of the reactants and the conditions utilized, such as with or without an organic solvent, etc., as previously discussed.

The halogenated organic silanes made in accordance with the practice of the present invention can be hydrolyzed to a variety of valuable intermediates such as silarylene silane diols and silarylene siloxane polymers obtained therefrom, bis(siloxane anhydrides), bis(siloxane imides), etc.

In order that those skilled in the art will be better able to practice the present invention, the following examples are given by way of illustration and not by way of limitation. All parts are by weight.

EXAMPLE 1

A mixture of 20 grams ($9.5-10^{-2}$ moles) of trimellitic anhydride acid chloride and 23 grams (0.1 mole) of 1,1,2,2-tetrachlorodimethyldisilane was heated with stirring under an atmosphere of dry nitrogen until a homogeneous solution resulted which was at a temperature of approximately 135° C. A cocatalyst mixture of 123 milligrams (0.5 mole percent) bis(benzonitrile)palladium chloride and 250 milligrams (1 mole percent) triphenylphosphine was then introduced, resulting in the formation of a red solution and a generation of carbon monoxide which was allowed to evolve from the reaction mixture. The reaction temperature was maintained between 140°-150° C. and methyltrichlorosilane was continually removed from the reaction. After two hours, a quantitative yield of methyltrichlorosilane (14.1 gram) was obtained. The reaction mixture was then distilled and there was obtained 10 grams or a 41% yield of 4-dichloromethylsilylphthalic anhydride having a boiling point of 170°-174° C., 0.01 torr. It was a clear viscous oil. The identity of the product was further confirmed by its NMR and IR spectra. Elemental analysis showed; Calc. $C_9H_6O_3SiCl_2$ 259.9463, Found 259.9464.

Two grams of the 4-dichloromethylsilylphthalic anhydride was dissolved in 20 ml of methylene chloride and the resulting solution was added to 20 ml of water. The resulting mixture was rapidly stirred for 2 hours. There was obtained a transparent glassy solid after the organic phase was recovered and the organic solvent evacuated from the resulting material for 30 minutes at 120° C. The resulting product was a methylsiloxane resin having chemically combined phthalic anhydride groups attached to silicon based on IR analysis. The methylsiloxane resin is useful as a coupling agent for making composites.

EXAMPLE 2

A mixture of 10 grams ($4.76 \times 10^{-2}$ mole) of trimellitic anhydride acid chloride and 9 grams ($5 \times 10^{-2}$ mole) of 1,2-dichlorotetramethyldisilane was heated under an atmosphere of dry nitrogen until a homogeneous solution was obtained at about 135° C. A cocatalyst consisting of 91 milligrams (0.5 mole percent) of bis(benzonitrile)palladium chloride and 124 milligrams (1.0 mole percent) triphenylphosphine was then introduced. The resulting solution was bright red and carbon monoxide separated from the mixture upon addition of the catalyst. Dimethyldichlorosilane having a boiling point of 70° C. was continuously removed until 5.8 grams was collected. There was obtained an 97% yield of product. Based on method of preparation the product was dimethylchlorosilylphthalic anhydride. Its identity was further confirmed by its IR and NMR spectra.

A 50 ml tetrahydrofuran solution containing 0.43 ml of water was added to the dimethylchlorosilylphthalic anhydride. The resulting solution was stirred at room temperature for 3 hours under reduced pressure to remove HCl as it was formed. The tetrahydrofuran was evaporated and replaced with 100 ml of a 1:1 toluene/nonane solution. A crystalline solid was formed upon heating. The resulting solution was decanted from the colored oily material which contained the catalyst. Recrystallization provided 8.1 gram, or an 80% yield of 1,3-bis(4'-phthalic anhydride)tetramethyldisiloxane as a colorless needle-like material having a melting point of 134°–135° C. The resulting bis(siloxane anhydride is a valuable intermediate for making silicone polyimide block polymers which are valuable insulating and dielectric materials.

In accordance with the above procedure, a reaction mixture containing 1500 grams (7.13 moles) of trimellitic anhydride acid chloride and 1490 grams (7.48 moles) of 1,2-dichlorotetramethyldisilane was stirred neat at 145° C. under an atmosphere of nitrogen. When the mixture become homogeneous, 1.65 grams $(4.3 \times 10^{-3}$ moles, 600 ppm) of bis(benzonitrile)palladium chloride and 2.24 grams $(8.54 \times 10^{-3}$ moles, 1200 ppm) of triphenylphosphine were introduced. Vigorous evolution of carbon monoxide gas ensued with an accompanying exothermic reaction. External heat was decreased to maintain a constant reaction temperature between 140°–150° C. Dimethyldichlorosilane was continuously removed as it was formed from the reaction mixture having a boiling point of 69°–70° C. After 15 hours at 145°–150° C., evolution of gas ceased and gas chromatographic analysis showed a 93% conversion to 4-chlorodimethylsilylphthalic anhydride. The crude sample also contained a considerable amount of dimethyldichlorosilane which was removed under reduced pressure and condensed in a dry ice/acetone trap.

When a GC analysis indicated complete removal of volatile chlorosilanes, 2 liters of dry tetrahydrofuran was added to dissolve the oily product and 64.2 ml. of water was added dropwise over a 3 hour period while the solution was maintained at 25° C. Gaseous HCl was removed from the system under reduced pressure. After stirring at room temperature for 5 hours, the resulting product was precipitated from solution. The crude product was filtered and the filtrate solution was removed in vacuo giving a second fraction of product. Two portions were combined and dissolved in hot toluene. Cooling provided 1185 grams (78% isolated yield) of crystalline 1,3-bis(4'-phthalic anhydride)-tetramethyldisiloxane.

EXAMPLE 3

A mixture was heated to 140° C. under an atmosphere of dry nitrogen consisting of 1.0 gram (4.9 millimoles) of terephthaloyl chloride, 3.7 grams (19.6 millimoles) of 1,2-dichlorotetramethyldisilane, 187 milligrams (5 mole percent) of bis-(benzonitrile)palladium dichloride and 256 milligrams (10 mole percent) of triphenylphosphine. The mixture which was initially a yellow solution turned to a deep red color. After heating for 4 hours, there was obtained a quantitavie yield of 1,4-bis-(dimethylchloro)benzene which was shown by GC analysis. The identity of the 1,4-bis-(dimethylchloro)benzene was verified by comparison to an authentic sample prepared from the chlorination of 1,4-bis-(dimethylsilyl)-benzene with triphenylchloromethane in accordance with the procedure of Corey et al., JACS, 85, 2430 (1963).

EXAMPLE 4

A reaction mixture containing 10 gm $(6 \times 10^{-2}$ mole) of p-cyanobenzoyl chloride and 15 gm (1.25 mole equivalent) of 1,2-dichlorotetramethyldisilane was heated to 135° C. during which time the solution became homogeneous. A cocatalyst mixture containing 200 mg. bis(benzonitrile)palladiumdichloride (1 mole %) and 274 mg triphenylphosphine (2 mole %) was then introduced. Carbon monoxide gas evolution began immediately and the reaction was heated at 140° C. for 12 hours while dimethyldichlorosilane was continuously removed. Vacuum distillation gave 7 gm (60% isolated yield) of 4-chlorodimethylsilylbenzonitrile, bp. 93°/0.1 torr, m.p. 40°–43° C. The resulting chlorodimethylsilylbenzonitrile, in the form of a low melting high moisture sensitive solid was hydrolyzed to the corresponding 1,3-bis(4'-benzonitrile)tetramethyldisiloxane in the form of a colorless liquid. The identity of the disiloxane was further confirmed by its NMR and IR spectra.

EXAMPLE 5

A gravity flow continuous reactor was employed consisting of a heated and stirred dropping funnel, a heated, supported catalyst bed containing 2.0 gm, 10% palladium or activated carbon (total palladium) a vent, and 4.5% collection reservoir for carbon monoxide and volatile monomeric silanes respectively and a collection vessel for the silylated aromatic material. Trimellitic anhydride acid chloride (10 gm, $4.8 \times 10^{-2}$ moles) and 1,2-dichlorotetramethyldisilane (13 gm, $6.9 \times 10^{-2}$ moles) were placed in the dropping funnel which was stirred and heated to 140° C. during which time the solution became homogeneous. The mixture was then introduced to the catalyst bed, which was heated to 210° C., at the rate of 1 ml/5 min. Evolution of CO gas was observed and 3.5 gm of dimethyldichlorosilane (57% theoretical yield) was collected in the side reservoir. Analysis of the material collected in the bottom vessel showed it contained dimethyldichlorosilane, 77% 4-chlorodimethylsilylphthalic anhydride, and 12% unreacted trimellitic anhydride acid chloride. The total conversion was 89%.

EXAMPLE 6

A mixture of 2.93 grams $(2.1 \times 10^{-2}$ moles) of benzoyl chloride and 5 grams $(2.2 \times 10^{-2}$ moles) of 1,2-dichlorotetramethyldisilane was heated neat under an atmosphere of dry nitrogen to 140° C. A catalyst mixture of 8 milligrams $(2.08 \times 10^5$ moles, 1270 ppm.) of bis(benzonitrile) palladium chloride and 11 milligrams $(4.2 \times 10^{-5}$ moles, 2500 ppm.) triphenylphosphine was introduced resulting in the evolution of gaseous carbon monoxide. The reaction mixture was heated at 140° C. for 20 hours. The mixture was then distilled resulting in 2.46 grams (91% yield) of dimethyldichlorosilane b.p. 68°–72° C. and 3.12 grams (87% yield) of phenyldimethylchlorosilane b.p. 85°/20 torr.

EXAMPLE 7

Following the procedure of Example 6, a series of additional silylated aromatic organic materials were prepared resulting from the decarbonylation of arylacyl chloride as shown by the following equation:

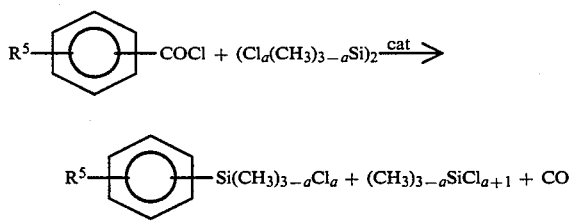

where $R^5$ and a are defined below.

| $R^5$ | a | conversion | % isolated yield |
|---|---|---|---|
| H | 1 | 85 | 89 |
| o-CH$_3$ | 1 | 17 | 13 |
| m-CH$_3$ | 1 | 100 | 47 |
| p-CH$_3$ | 1 | 100 | 58 |
| o-Cl | 1 | 50 | 25 |
| m-Cl | 1 | 83 | 73 |
| p-Cl | 1 | 75 | 86 |
| o-OMe | 1 | 100 | 32 |
| m-OMe | 1 | 87 | 71 |
| p-OMe | 1 | 61 | 52 |
| m-COCl | 1 (1 eq.) | 44 | 19 |
| m-COCl | 1 (1 eq.) | 86 | 61 |
| m-COCl | 1 (1 eq.) | 91 | 83 |
| o-COCl | 1 (2 eq.) | ND | ND |
| m-COCl | 1 (2 eq.) | b | 66 |
| p-COCl | 1 (2 eq.) | b | 63 |
| m-NO$_2$ | 1 | 100 | 74 |
| p-NO$_2$ | 1 | 100 | 72 |
| p-CN | 1 | 87 | 77 |
| 3,4 acid anhydride (trimellitic) | 1 | 100 | 83 |
| 3,4 acid anhydride N—butylimide (trimellitimide) | 1 | 100 | 81* | b run to complete conversion.
*yield determined by gas chromotography

EXAMPLE 8

A mixture of 100 grams (0.49 moles) of terephthaloylchloride and 116 grams (0.51 moles) of symmetrical tetrachlorodimethyldisilane was heated to 145° C. under an atmosphere of dry nitrogen. After the solution become homogeneous, 5.3 grams (0.1 mole percent) of palladium (12-30 mesh carbon, 1% percent loading) was introduced which initiated carbon monoxide evolution. Methyltrichlorosilane was continuously removed by maintaining the mixture at a temperature of 68°–71° C. After 24 hours at 145° C., a second catalyst batch of 5.3 grams was introduced followed by a similar loading after 48 hours. The mixture was heated for an additional 72 hours at 145° C. Fractional distillation of the mixture provided 62 grams (50% isolated yield of p-dichlоromethylsilylbenzoyl chloride, b.p. 126°/3 as a colorless liquid. Its identity was further confirmed by its NMR and IR spectra.

An ethereal solution containing 5 grams (1.97×10$^{-2}$ moles) of p-dichloromethylbenzoyl chloride and 50 ml. of solvent was stirred at room temperature which was added 0.4 ml. of water. The resulting mixture was stirred for 15 minutes at room temperature. Removal of the solvent resulted in 3.54 grams (92% isolated yield) of a silicone fluid containing pendent benzoyl chloride and methyl groups. The identity of product was further confirmed by its infrared spectra.

EXAMPLE 9

A mixture of 50 grams (0.25 mole) of terephthaloyl chloride and 116 grams (0.51 mole) of symmetrical tetrachlorodimethyldisilane was heated neat to 145° C. under an atmosphere of dry nitrogen. After the mixture became homogeneous, 10.6 grams (1 mole percent) of palladium on steam activated wood carbon 5% loading (4-8) mesh was introduced causing evolution of carbon monoxide. Methyltrichlorosilane was formed it was continuously removed by distillation, boiling point 68°–71° C. Completion of the reaction was determined gas chromatographic analysis. Fractional distillation gave 1,4-bis-dichloromethylsilylbenzene.

EXAMPLE 10

A reaction mixture containing 20 grams (7.43×10$^{-2}$ moles) of hexachlorodisilane and 15.7 grams (7.43×10$^{-2}$ moles) of trimellitic anhydride acid chloride was heated neat under an atmosphere of dry nitrogen to 145° C. When the mixture become homogeneous, 1.58 grams (1 mole percent) of palladium on steam activated wood carbon (4-8 mesh, 5% loading) was introduced causing evolution of carbon monoxide The entire mixture was then heated to 145°–150° C. for 10 hours.

After cooling the catalyst was removed by filtration and distillation of the filtrate gave a substantial yield of 4-trichlorosilylphthalic anydride. The identity of the compound was further confirmed by its IR spectra and mass spectra.

Although the above examples are directed to only a few of the very many variables which can be utilized in the practice of the silylation method of the present invention, it should be understood that the present invention is directed to the use of a much broader variety of halogenated polysilanes as shown by formula (1), aromatic acyl halide as shown by formula (2) and transition metal catalyst as shown in the description preceding these examples.

What I claim as new and desire to secure by Letters Patent of the United States is:

1. A method for making organic silanes which comprises
    (A) effecting reaction between aromatic acyl halide of the formula

and halogenated polysilane of the formula

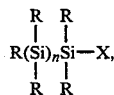

in the presence of an effective amount of a transition metal catalyst, and
    (B) thereafter recovering organic silane from the resulting mixture of (A), where X is a halogen radical, R is selected from X, hydrogen, $C_{(1-13)}$ monovalent hydrocarbon radicals, substituted $C_{(1-13)}$ monovalent hydrocarbon radicals and divalent —O—, —S— radicals and mixtures thereof, which can form ≡SiOSi≡ and ≡SiSSi≡ connecting groups, $R^1$ is a $C_{(6-20)}$ monovalent or polyvalent aromatic organic radical, n is an integer equal to 1 to 50 inclusive, and m is an integer equal to 1 to 4 inclusive.

2. A method in accordance with claim 1, where the halogenated polysilane is 1,1,2,2-tetrachlorodimethyldisilane.

3. A method in accordance with claim 1, where the aromatic acyl halide is trimellitic anhydride acid chloride.

4. A method in accordance with claim 1, where the aromatic acyl halide is terephthaloyl chloride.

5. A method in accordance with claim 1, where the halogenated polysilane is 1,2-dichlorotetramethyldisilane.

6. A method in accordance with claim 1, where the transition metal catalyst is a cocatalyst consisting of bis(benzonitrile)palladium chloride and triphenylphosphine.

7. A method in accordance with claim 1 conducted in a continuous manner.

8. A method in accordance with claim 1, where the transition metal catalyst is palladium on carbon.

9. An organic silane selected from the class consisting of 2-chlorodimethylsilylbenzoylchloride 2-dichloromethylsilylbenzoylchloride, 2-trichlorosilylbenzoylchloride, 3-chlorodimethylsilylbenzoylchloride, 3-dichlorosilylbenzoyl chloride, 3-trichlorosilylbenzoyl chloride, 4-dichloromethylsilylbenzoylchloride, 4-trichlorosilylbenzoylchloride.

10. 2-chlorodimethylsilylbenzoylchloride in accordance with claim 9.

11. 2-dichloromethylsilylbenzoylchloride in accordance with claim 9.

12. 2-trichlorosilylbenzoylchloride in accordance with claim 9.

13. 3-chlorodimethylsilylbenzoylchloride in accordance with claim 9.

14. 3-dichloromethylsilylbenzoylchloride in accordance with claim 9.

15. 3-trichlorosilylbenzoylchloride in accordance with claim 9.

16. 4-dichloromethylsilylbenzoylchloride in accordance with claim 9.

17. 4-trichlorosilylbenzoylchloride in accordance with claim 9.

18. Chlorosilylphthalic anhydrides having the formula

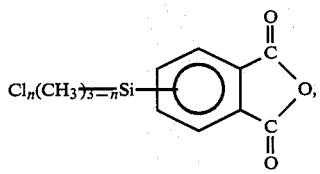

where n is equal to 1 to 3 inclusive.

19. The compound

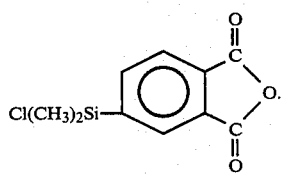

20. The compound

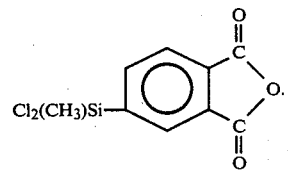

21. The compound

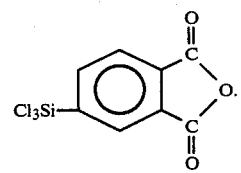

22. Chlorodimethylsilylbenzonitriles having the formula

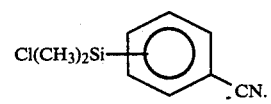

23. A method in accordance with claim 1, where the aromatic acylhalide is nitrobenzoylchloride.

24. A method in accordance with claim 1, where the aromatic acylhalide is cyanobenzoylchloride.

25. A method in accordance with claim 1, where the aromatic acylhalide is N-n-butyltrimelitic imide acid chloride.

26. A method in accordance with claim 1, where the aromatic acylhalide is allylchloride.

27. A method in accordance with claim 1, where the aromatic acylhalide is isophthaloylchloride.

28. A method for making organic silane in accordance with claim 1 having the formula,

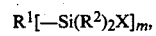

where X is a halogen radical, hydrogen, $R^1$ is a $C_{(6-20)}$ monovalent or polyvalent aromatic organic radical selected from hydrocarbon radicals and substituted hydrocarbon radicals, $R^2$ is selected from $C_{(1-13)}$ monovalent hydrocarbon radicals, substituted $C_{(1-13)}$ monovalent hydrocarbon radicals, and mixtures thereof, n is an integer equal to 1–15 inclusive, and m is an integer equal to 1–4 inclusive.

29. A method in accordance with claim 28, where the organic silane has the formula,

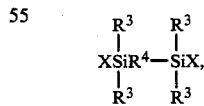

where X is a halogen radical, $R^3$ is selected from $C_{(1-13)}$ monovalent hydrocarbon radicals, substituted $C_{(1-13)}$ monovalent hydrocarbon radicals, and mixtures thereof, and $R^4$ is a member selected from the class consisting of $C_{(6-13)}$ divalent aromatic radicals, and substituted $C_{(6-13)}$ divalent aromatic radicals.

30. The method of claim 1 where 1,4-(bis-chlorodimethylsilyl)benzene is produced.

* * * * *